United States Patent [19]

Söderberg et al.

[11] Patent Number: 5,415,865
[45] Date of Patent: May 16, 1995

[54] MEANS HAVING MICROBIAL EFFECT AND LITTLE OR COMPLETELY ABOLISHED TENDENCY TO DEVELOP CONTACT ALLERGIC REACTIONS OR TOXIC EFFECTS AND USE THEREOF IN E.G. SKIN AND WOUND TREATMENT PRODUCTS

[75] Inventors: Thor Söderberg; Stig Holm; Göran Hallmans, all of Umeå, Sweden

[73] Assignee: Molnlycke AB, Gothenburg, Sweden

[21] Appl. No.: 299,083

[22] Filed: Aug. 18, 1994

Related U.S. Application Data

[63] Continuation of Ser. No. 938,220, Oct. 14, 1992, abandoned.

[30] Foreign Application Priority Data

Apr. 24, 1990 [SE] Sweden ............... 9001475

[51] Int. Cl.⁶ ........................... A61F 13/00
[52] U.S. Cl. ................... 424/445; 424/196.1; 424/447; 424/448; 424/614
[58] Field of Search ............. 424/445, 447, 448, 614, 424/196.1

[56] References Cited

U.S. PATENT DOCUMENTS

| | | | |
|---|---|---|---|
| 4,172,123 | 10/1979 | Lowicki | 424/47 |
| 4,460,369 | 7/1984 | Seymour | 424/448 |
| 4,937,066 | 6/1990 | Vlock | 424/614 |
| 5,100,671 | 3/1992 | Maeda | 424/445 |

FOREIGN PATENT DOCUMENTS

| | | |
|---|---|---|
| 0272349 | 12/1963 | Australia . |
| 0153915 | 9/1985 | European Pat. Off. . |
| 57-158724 | 9/1982 | Japan . |
| 59-67219 | 4/1984 | Japan . |
| 62-63518 | 3/1987 | Japan . |
| 1395815 | 5/1975 | United Kingdom . |

OTHER PUBLICATIONS

Grant and Hackh's Chemical Dictionary, 5th ed, pp. 1, 146, 452 and 510 1989.

*Primary Examiner*—D. Gabrielle Phelan
*Attorney, Agent, or Firm*—Young & Thompson

[57] ABSTRACT

An agent which possesses antimicrobial properties and a minimum tendency, or a completely discontinued tendency, to produce contact allergic reactions or toxic effects includes a mixture of a compound which produces $Zn^{2+}$-ions and one or more so-called resin acids or other resin compounds or resin acid derivatives present in the purest possible form, and to the use of the agent in preparing skin, wound, teeth and mucus-membrane treatment products, and to such products as insulating material, building material, paper, surface treatment material, disinfectants, cosmetics and like products which contain conventionally different types of resins.

4 Claims, 3 Drawing Sheets

① ABIETIC ACID
② DEHYDROABIETIC ACID
③ NEOABIETIC ACID
④ PIMARIC ACID
⑤ LEVOPIMARIC ACID
⑥ ISOPIMARIC ACID
⑦ PALUSTRINIC ACID

① 0.078
② 0.0157
③ 0.314
④ 0.629
⑤ 1.258
⑥ 2.516

MEANS HAVING MICROBIAL EFFECT AND LITTLE OR COMPLETELY ABOLISHED TENDENCY TO DEVELOP CONTACT ALLERGIC REACTIONS OR TOXIC EFFECTS AND USE THEREOF IN E.G. SKIN AND WOUND TREATMENT PRODUCTS

This application is a continuation of application Ser. No. 07/938,220, filed Oct. 14, 1992, now abandoned.

FIELD OF THE INVENTION

The invention relates to an agent that possesses antimicrobial properties and exhibits a minimum tendency, or a completely discontinued tendency, to generate contact allergic reactions or toxic effects. The invention relates in particular to an agent which because of its antimicrobial properties is suitable for use as a curative constituent of products intended for the treatment of the skin, wounds and mucus-membrane, for example wound dressings and the like, and also for use in, for instance, rinsing solutions for medical use. The invention also relates to the use of said agent in the manufacture of such products, such as the manufacture of wound dressings or the like, or in the manufacture of a rinsing solution for medicinal use.

BACKGROUND ART

Zinc compounds have long been used in the treatment of wounds. The bacteria-inhibiting and local-drying properties of zinc are well known. Colophony has also been earlier used for its bacteria-inhibiting properties.

Colophony is obtained from certain Pinus species and consists of about 90% free resin acids, with the remainder consisting of neutral substances, oxidized terpentines and minor quantities of esters and anhydrides, depending upon the origin of the colophony. The resin acids are a group of mono-basic carboxylic acids, all with a phenanthrene skeleton and all having 20 carbon atoms in the molecule. With two exceptions, dextropimaric acids, the resin acids exhibit the same substituents in the same positions and differ only with respect to the number and the positions of the double bonds.

It is also known to use zinc compounds in combination with colophony in, for instance, zinc tape intended for wound care. MEZINC® (from Mönlycke AB), which is an occlusive dressing consisting of cotton fabric coated with PVC and an adhesive substance consisting of rubber, mineral oils, colophony and Zn O possesses good bacteria inhibiting properties against various bacterial strains. In this case, zinc compounds and colophony are used for their respective bacteria inhibiting effect and colophony is also used as a mediator for the transportation of zinc ions to tissue and, in the adhesive substance, also for its adhesive properties.

One disadvantage with the use of adhesive products which contain zinc compounds in combination with colophony is that these products engender contact-allergic reactions in many people, which has reduced the use of these adhesive products. It is true that when used, the zinc present in the adhesive product will neutralize or inactivate the major part of the colophony present. The contact allergic reactions remain, however, to a large extent.

It is known from Patent Abstract of Japan, Vol. II, No. 262, C-442, abstract of JP62-63518, publ. 20th Mar. 1987 and Patent Abstract of Japan, Vol. 8, No. 8, C-236, abstract of JP59-67219, publ. 16th Apr. 1984, that substances or products which contain abtic acid or dehydroabietic acid and/or dihydroabietic acid are effective against passive cutaneous anaphylaxis (PCA), which is a rapid hypersensitive reaction (anaphylactic) which manifests itself in hayfever, urticaria, argio neurotic oedema, atopic eczema, anaphylactic shock or skin rashes within a period of about 10 to 20 minutes. This anaphylactic effect shall be held separate from another type of allergic condition with which the present invention is concerned, namely the classic contact eczema which is effectuated through direct contact between immune cells and cells which have the allergen bound to their surfaces and not by humoral antibodies, this reaction developing within about 12 to 48 hours. The two publications cited above are not concerned with contact allergies but alledge an inhibiting effect of the acids against PCA.

OBJECT OF THE INVENTION

The object of the invention is to attempt to eliminate the drawbacks associated with known zinc-colophony-based adhesive products and the like and to provide a product which while affording a pronounced bacteria-inhibiting effect will not induce pronounced contact-allergic reactions.

SUMMARY OF THE INVENTION

This object is surprisingly achieved in accordance with the invention by substituting colophony of conventional zinc-colophony products with one or more substantially pure resin acids, such as abietic acid, dehydroabietic acid, neoabietic acid, pimaric acid, levopimaric acid, isopimaric acid and palustrinic acid or resin acid derivatives, such as dehydroabietylamine. As will be evident from the following, it has been found that such a combination exhibits splendid antimicrobial properties and that both the contact-allergic and the toxic effect have been suppressed to a large extent. The exudation or release of zinc from, for instance, adhesive product to serum through the agency of the acid is improved furthermore.

This was surprising, since the same acids, although in an impure form and together with other substances, are present in colophony, which exhibits pronounced contact-allergic and toxic effects. Although no simple explanation can be given as to why this is so, it is obvious that the purity of the acids is significant to the good effect achieved. The acid or acids present in the agent shall have the purest possible form and preferably be at least 98% pure, and even more preferably at least 99% pure. However, the aforesaid effects have also been obtained with acids having a purity of about 40–60%. As will be seen from the following test reports on the resin acids used, dehydroabietic acid has been found to be the best of these acids because it provides the best bacteria inhibiting and toxicity lowering low-allergenic effect when used together with zinc. The zinc component may be present in the form of a compound which produces $Zn^{2+}$-ions when the agent is used to treat wounds. Zn O is the most usual compound, although salts with inorganic acids, such as Zn $SO_4$ and Zn $Cl_2$ can also be used to the same effect.

The zinc component and the acid component are preferably present in the inventive agent in proportions of at least about 1:2 and at most of about 20:1, based on the weight of zinc components as Zn O and on the pure acid component. When proportions greater than about 20:1 are used, the effect of the acid component on the agent when treating wounds is excessively low, whereas proportions lower than about 1:2 do not improve the effect of the agent and the agent becomes unnecessarily expensive, because the acid is much more expensive than the zinc component and the release of zinc through the intermediary of the acid is affected negatively.

The aforesaid properties of the inventive agent render the agent particularly suitable for use in different skin and wound treatment products, and also in products intended for the treatment of mucus-membrane, such as mouth mucus-membrane, stomach mucus-membrane and intestinal mucus-membrane. Accordingly, the invention also relates to the use of the inventive agent in the preparation of such a product, for example a wound care product. An example of one such product is an adhesive wound dressing whose manufacture includes the use of conventionally used components, such as solvent, mineral oil, rubber solution, etc., for instance. In addition, the agent can also be used in building materials (fibreboard), insulating materials, paper, and surface treating materials (such as paints), thereby greatly improving such products with respect to their antimicrobial, contact-allergic and toxic effects. In this regard, calcium and magnesium ions may also be included, these ions playing the same part as the zinc ions.

BRIEF DESCRIPTION OF THE DRAWINGS

The invention will now be described in more detail with reference to the accompanying drawings, in which.

Antimicrobial/Antibibacterial) Effect

Figure 1A:
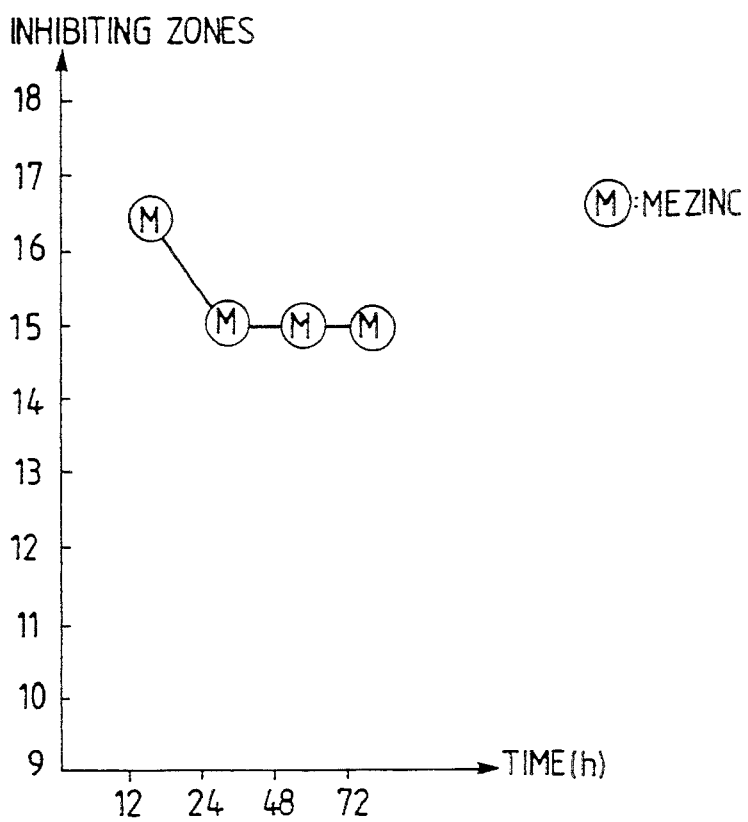
FIG. 1A shows the antimicrobial effect in the form of inhibiting zones in mm as a function of time in the case of the known zinc and colophony combination.
Figure 1B:
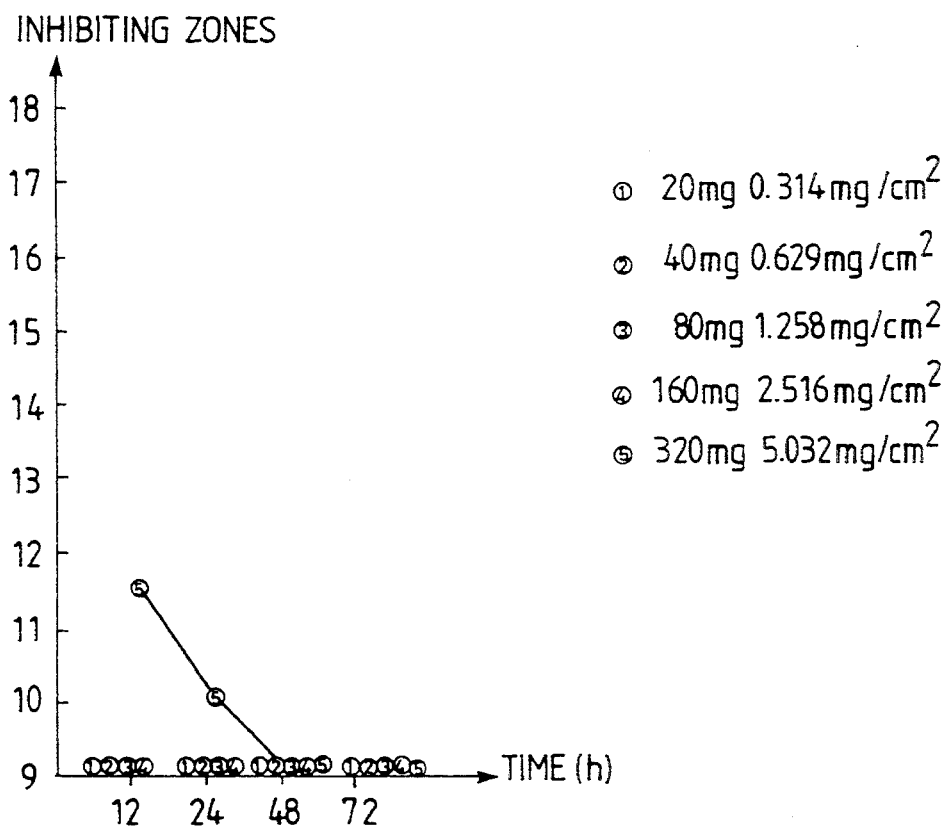
FIG. 1B illustrates the effect achieved when solely zinc is present in various concentrations, in the absence of an acid component.
Figure 1C:
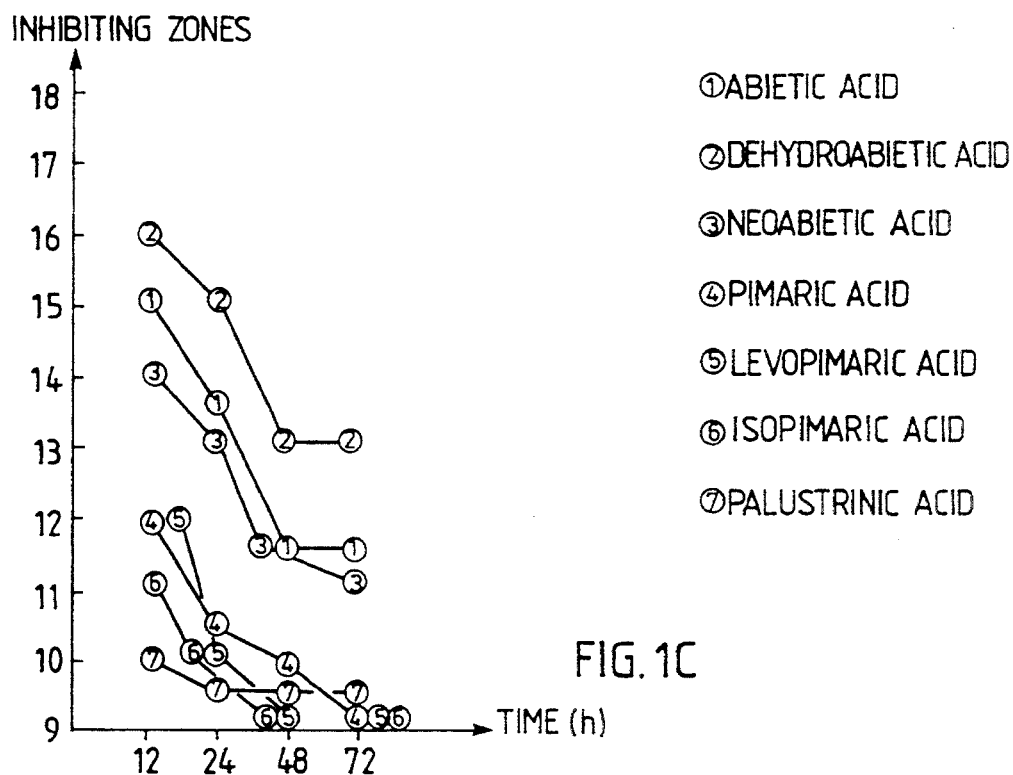
FIG. 1C illustrates the effect obtained when using seven different resin acids in accordance with the invention.
Figure 1D:
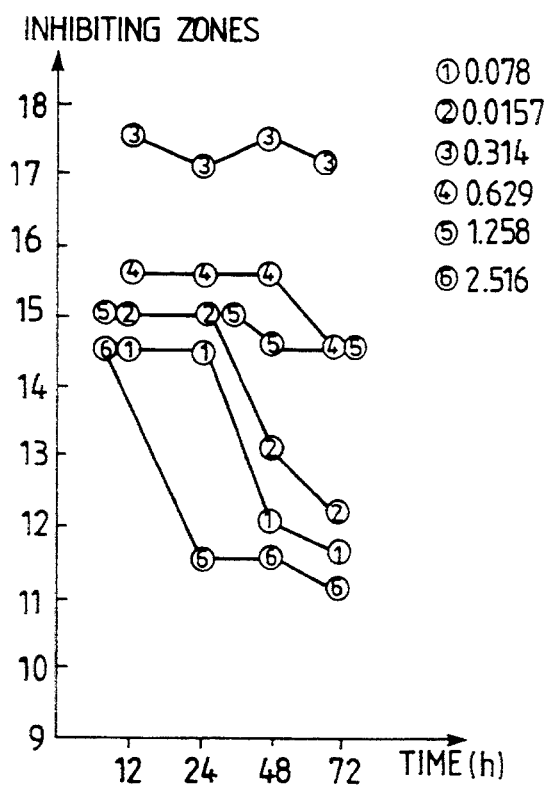
FIG. 1D illustrates the effect obtained when using a combination of zinc oxide and abietic acid in accordance with the invention, in different weight ratios.
Figure 1E:
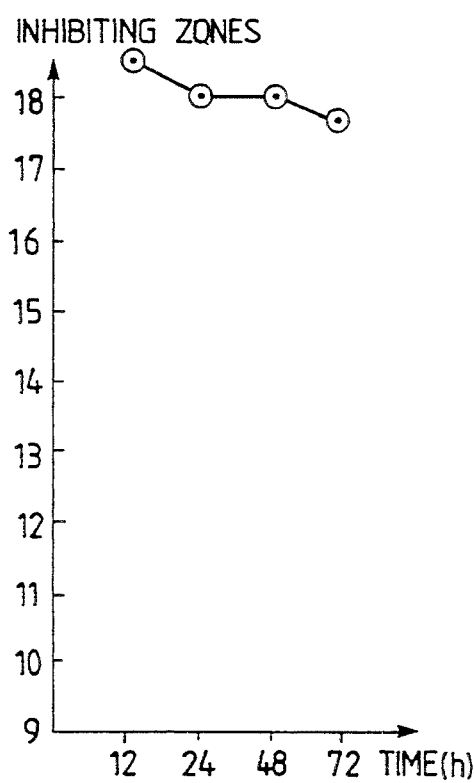
FIG. 1E illustrates the effect obtained when using a combination of zinc oxide and dehydroabietic acid in accordance with the invention in a mixing ratio of 16:1.

The nature of the experiment:

0.1 ml of a suspension $(1.10^5)$ bacteria/ml) of bacteria (Staphylococcus Aureus S-209) in log-phase-growth were spread with the aid of glass beads over an agar plate in a plastic tray, such as to obtain uniform growth. An adhesive product in the form of pieces of adhesive tape were applied in a circular pattern to the agar gel, with the aid of sterilized pincettes. Incubation was effected in a heated cabinet at 37° C. The inhibition zones were recorded for a full test series after 12, 24, 48 and 72 hours, with the aid of an mm-graduated rule placed against the edges of the plastic tray, with an eye-distance to the tray of about 40 cm and at an accuracy of 0.5 mm.

a) There was first tested an adhesive product comprising the known product MEZINC$^R$ (Mölnlycke AB) containing zinc oxide (2.4 mg/cm$^2$), colophony (3.04 mg/ cm$^2$) and natural rubber (2.28 mg/cm$^2$). The result recorded is shown in FIG. 1A.

b) Also tested was an adhesive product which contained Zn O in various concentrations, but no resin acid component at all. The result is illustrated in FIG. 1B.

c) Seven mutually different adhesive products were tested, each containing 1.258 mg/cm$^2$ of abietic acid, dehydroabietic acid, neoabietic acid, pimaric acid, levopimaric acid, isopimaric acid and palustrinic acid respectively. The results are given in FIG. 1C.

d) Also tested was an adhesive product containing zinc oxide and abietic acid in the weight ratios of 2:1, 4:1, 8:1, 16:1, 32:1 and 64:1. The results are set forth in FIG. 1D.

e) Also tested was an adhesive product containing Zn O and dehydroabietic acid in the weight ratio of 16:1. The results are seen in FIG. 1E.

Conclusion

The results of these experiments or tests show that a) solely Zn O fails to provide a particularly high antibacterial effect, b) that the individual acids provide a much higher antibacterial effect, and c) that the combination of highly pure acid and zinc oxide provides an antibacterial effect which is at least equal to the effects obtained with an adhesive product that contains colophony and zinc oxide.

Allergic Effect

Test method: A so-called patch test was carried out while using Finn Chambers ® (Fregert S. Manual of Contact Dermatitis, 2nd ed., Copenhagen: Munksgaard 1981; 71–81) on a total of 14 patients suffering from known contact allergy against colophony. Highly pure resin acids, namely abietic acid (90–95% pure), dehydroabietic acid (>99%) and isopimaric acid (>99%) (from Helix Biotech Ltd., Richmond, B.C., Canada) were tested. The reactions against the actual adhesive product itself (the same as MEZINC ®), against the zinc oxide and against the pure resin acids were established and are set forth in the following Table 1.

TABLE 1

PATIENTS WITH POSITIVE PATCH-TEST-REACTIONS AGAINST PURE RESIN ACIDS (10%) OF 14 PATIENTS WITH KNOWN CONTACT ALLERGY AGAINST COLOPHONY.

| | PATIENT No | | | | | | | | | | | | | | TOT. |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | |
| ABIETIC ACID (10%) | + | − | − | + | − | + | − | − | + | − | + | − | + | + | 7 |
| NEOABIETIC ACID (10%) | + | − | − | − | − | − | − | − | + | − | − | − | + | − | 3 |
| DEHYDROABIETIC ACID (10%) | − | − | − | − | − | − | − | − | − | − | − | − | − | − | 0 |
| ISOPIMARIC ACID (10%) | − | − | − | − | − | − | − | − | − | − | − | − | − | − | 0 |

TABLE 1-continued

PATIENTS WITH POSITIVE PATCH-TEST-REACTIONS AGAINST PURE RESIN ACIDS (10%) OF 14 PATIENTS WITH KNOWN CONTACT ALLERGY AGAINST COLOPHONY.

| | PATIENT No | | | | | | | | | | | | | | TOT. |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | |
| LEVOPIMARIC ACID (10%) | − | − | − | − | − | − | − | − | − | − | − | − | − | − | 0 |
| ADHESIVE PRODUCT 10% (FROM MEZINC ®) | − | − | + | − | + | − | − | − | − | + | − | − | − | − | 3 |
| ZINC OXIDE (10%) | − | − | − | − | − | − | − | − | − | − | − | − | − | − | |

− NEGATIVE
+ ERYTHEMA AND INFILTRATION OR ERYTHEMA, INFILTRATION AND PAPULES OR VESICLES

Conclusion: The allergy tests showed that out of 14 patients with known contact allergy against colophony, very few showed any of the same allergic reaction against highly pure individual acids and zinc oxide. This shows the superior effect of an agent produced in accordance with the invention.

Toxic Effect

The cytotoxic effect in vitro was studied for dehydroabietic acid, a representative compound used in accordance with the invention, on human polymorphoneuclear leucocytes (PMN-cells) while measuring the leakage of $^{51}$Cr from labelled cells. In these tests, cell membrane damage was manifested in an increase in plasma membrane permeability, resulting in an increased leakage of cytoplasmic localized $^{51}$Cr.

Preparation of PMN cells for the purpose of assessing cytotoxicity: Venous blood was taken from adult volunteers in acid-citrate-dextrose-tubes. The granulocytes were isolated from the erythrocytes by dextran sedimention, essentially in accordance with Babior and Cohen (Cline M. J. (ed): Leucocyte function: New York: Churchill-Livingstone, 1981:1–38). The leucocytic cell mass was centrifuged at 160×g for 10 minutes at 4° C. The supernatant liquid was thrown away and remaining erythrocytes were eliminated by adding ice cold distilled water. After 30 seconds the toxicity was re-established with ice cold 0.6M Na Cl. The cells were washed three times (160×g, for 5 minutes at 4° C.) and finally dispersed in ice cold RPMI, $10^7$ cells/mi. 90% of the cell suspension consisted of PMN-cells.

The cell suspension was incubated with Na $^{51}$Cr RO$_4$ (90 µCi/ml, de Pont de Nemours, Dreieich, Federal Republic of Germany) for 60 minutes at 37° C., washed four times (160×g, 5 minutes at 4° C.) and dispersed in modified GBSS (see below) to $10^7$ cells/ml.

The zinc source used was a filtrate of Zn O produced by preparing a zinc oxide suspension of 179 mg Zn O (Merck, Darmstadt, Federal Republic of Germany) and 100 ml of modified Gey's solution (modified GBSS consisting of 8 g Na Cl, 0.37 g KCl, 0.07 g MgSO$_4$·7-H$_2$O, 0.21 g MgCl$_2$·6H$_2$O, 0.22 g MgCl$_2$·2H$_2$O, 1.0 g glucose and 2.38 g HEPES added with 1000 ml water, pH 7.3) and stirred for 20 hours at 37° C. The suspension was passed through a 0.2 µm membrane filter and the filtrate was used in the experiment. Dehydroabietic acid (DHAA) was used in the form of a storage solution of DHAA (purity >99% from Helix Biotech Ltd., Vancouver, B.C., Canada) prepared by dissolving 100 mg DHAA in 1 ml of 99% ethanol.

The test solutions were prepared 30 minutes prior to adding the PMN-cells and consisted of DHAA: 0–500 µg/ml, with and without zinc oxide as the aforesaid filtrate, 300 µmol/l.

50 µl of $^{51}$Cr labelled PMN-cells were mixed with 100 µl of the test solutions on a fabric cultivating plate having 96 wells (Linbro Flow Lab) in triple arrays. Six wells on each plate were used without a DHAA addition, with or without zinc oxide filtrate, as a comparison test. Subsequent to filling the wells with the test solutions, the plates were incubated for 60 minutes at 37° C., and were then centrifuged at 500×g for 5 minutes and the radio activity (counts per 120 s) was measured in 75 µl supernatant liquid in a gamma-scintillation spectrometer (Auto-gamma Scintillation Spectrometer Packard). The percentual release of $^{51}$Cr, indicating cell membrane damage, was calculated with the aid of the following equation:

$$\% \text{ cytotoxicity} = \frac{\text{leakage} - \text{spontaneous leakage}}{\text{maximum leakage} - \text{spontaneous leakage}} \cdot 100$$

Spontaneous leakage never exceeded 10% of maximum leakage.

Figure 2:
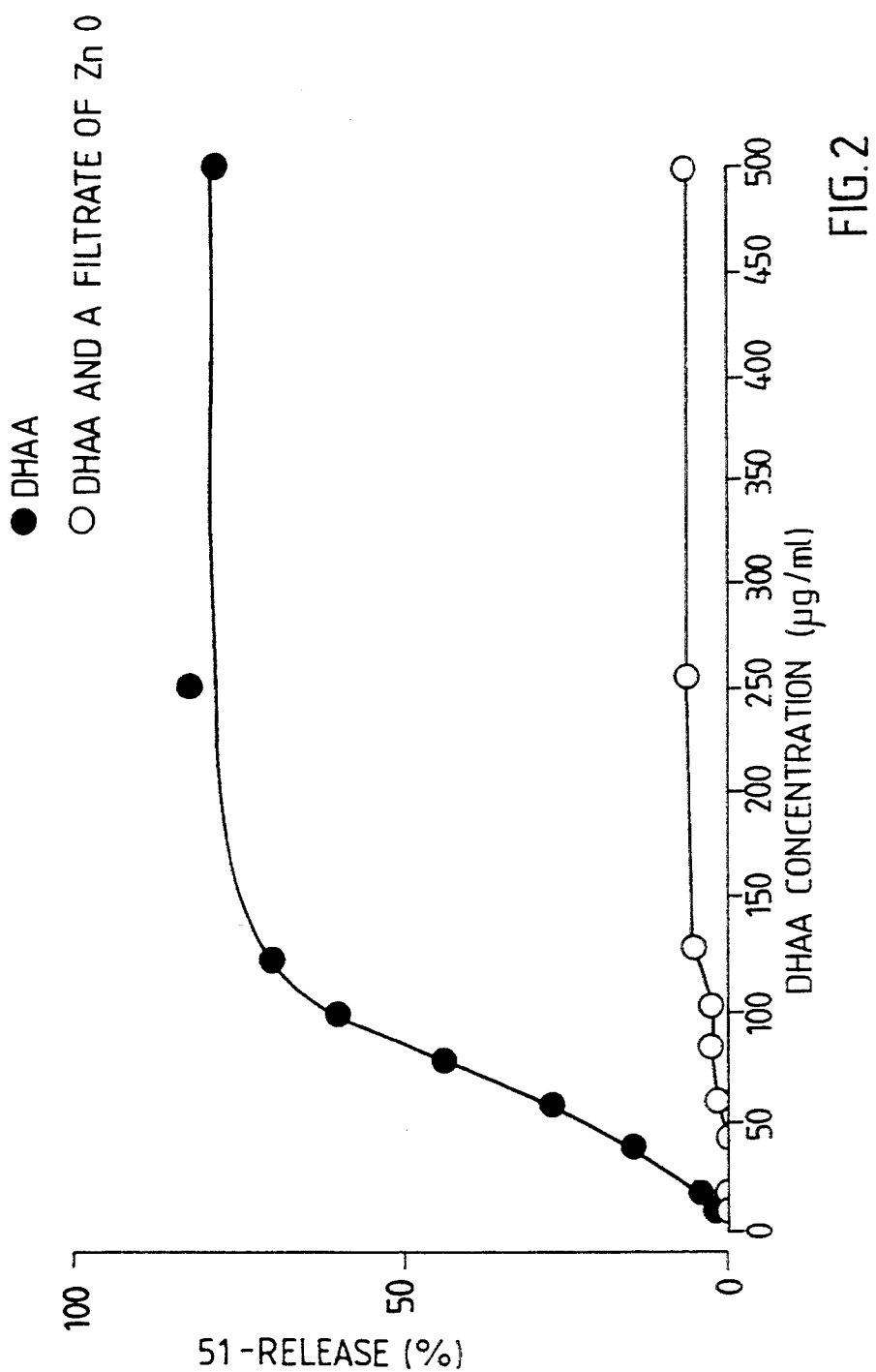
FIG. 2 illustrates cytotoxicity expressed as $^{51}Cr$-leakage as a function of the amount of dehydroabietic acid (DHAA) present with and without the presence of a zinc component.

The result: The result is set forth in FIG. 2. Toxic effects on the PMN-cells were observed at low concentrations of DHAA (20 µg/ml). A marked increase in toxicity was then observed up to 250 µg/ml DHAA. When the zinc oxide filtrate was used together with DHAA, no toxic effect of DHAA was observed up to 100 µg/ml. Only slight toxicity was registered from about 125 µg/ml.

Thus, in summary, the inventive agent exhibits splendid, unexpected properties which render the agent well suited for use in different skin, wound and mucus-membrane treatment products and also in such products as building material (fibreboard and insulating material), paper and surface treatment materials (paints and the like).

We claim:

1. An agent having an antimicrobial effect and no or a minimum tendency of producing contact allergic reactions or toxic effects, wherein the agent consists essentially of a mixture of a) a compound which produces $Zn^{2+}$-ions and b) resin acid of at least 90% purity selected from the class consisting of dehydroabietic acid, neoabietic acid, pimaric acid, levopimaric acid, isopimaric acid, palustrinic acid and dehydroabiethylamine, in a weight ratio of the compounds a) and b) of between 1:2 and 20:1, calculated on $Zn^{2+}$ as zinc oxide and on pure component b).

2. Wound dressing, having a layer comprising an agent consisting essentially of a mixture of a) a compound which produces $Zn^{2+}$-ions and b) resin acid of at least 90% purity selected from the class consisting of dehydroabietic acid, neoabietic acid, pimaric acid, levopimaric acid, isopimaric acid, palustrinic acid, and dehydroabiethylamine, in a weight ratio of the components a) and b) of between 1:2 and 20:1, calculated on $Zn^{2+}$ as zinc oxide and on pure component b).

3. An agent according to claim 1, wherein said resin acid is of at least 98% purity.

4. A wound dressing according to claim 2, wherein said resin acid is of at least 98% purity.

* * * * *